(12) United States Patent
Lei

(10) Patent No.: US 12,428,443 B2
(45) Date of Patent: Sep. 30, 2025

(54) ABIRATERONE PRECURSOR COMPOUND AND PREPARATION METHOD AND USE THEREOF

(71) Applicant: SUZHOU AIHE PHARMACEUTICAL TECHNOLOGY CO., LTD., Suzhou (CN)

(72) Inventor: Haoyan Lei, Suzhou (CN)

(73) Assignee: SUZHOU AIHE PHARMACEUTICAL TECHNOLOGY CO., LTD., Suzhou (CN)

(*) Notice: Subject to any disclaimer, the term of this patent is extended or adjusted under 35 U.S.C. 154(b) by 50 days.

(21) Appl. No.: 18/685,899

(22) PCT Filed: Aug. 25, 2022

(86) PCT No.: PCT/CN2022/114763
§ 371 (c)(1),
(2) Date: Feb. 23, 2024

(87) PCT Pub. No.: WO2023/025241
PCT Pub. Date: Mar. 2, 2023

(65) Prior Publication Data
US 2024/0279269 A1    Aug. 22, 2024

(30) Foreign Application Priority Data
Aug. 26, 2021  (CN) .......................... 202110985807.5

(51) Int. Cl.
C07J 43/00    (2006.01)
A61K 31/58    (2006.01)

(52) U.S. Cl.
CPC .............. C07J 43/003 (2013.01); A61K 31/58 (2013.01)

(58) Field of Classification Search
None
See application file for complete search history.

(56) References Cited

U.S. PATENT DOCUMENTS

| | | | |
|---|---|---|---|
| 2015/0337003 A1 | 11/2015 | Koziol et al. | |
| 2017/0216443 A1* | 8/2017 | Sun ........................ | A61K 31/58 |

FOREIGN PATENT DOCUMENTS

| | | |
|---|---|---|
| CN | 104017045 A | 9/2014 |
| CN | 105037478 A | 11/2015 |
| CN | 105646637 A | 6/2016 |
| CN | 106977577 A | 7/2017 |
| CN | 113527401 A | 10/2021 |

OTHER PUBLICATIONS

Translation of the claims of CN 105646637. Retrieved from Espacenet on May 29, 2024, https://worldwide.espacenet.com/patent/search/family/056073638/publication/CN105646637A?q=cn105646637. Published 2016. (Year: 2016).*
Translation of CN106977577, published 2017. Retrieved from Google Patents on Jul. 29, 2024, https://patents.google.com/patent/CN106977577A/en?oq=cn106977577. (Year: 2017).*
Translation of claims, CN 105646637, published 2016. Retrieved from Espacenet on Jul. 29, 2024, https://worldwide.espacenet.com/patent/search/family/056073638/publication/CN105646637A?q=cn105646637 (Year: 2016).*

* cited by examiner

Primary Examiner — James H Alstrum-Acevedo
Assistant Examiner — Lauren Wells
(74) Attorney, Agent, or Firm — Bayramoglu Law Offices LLC

(57) ABSTRACT

A precursor compound of abiraterone, and a preparation method and use thereof are provided. The compound has a structure represented by a formula I. The present disclosure also provides a preparation method of the compound represented by the formula I, a hydrochloride salt of the compound represented by the formula I and a preparation method thereof, and uses of the compound and the hydrochloride salt in preparation of a 17α-hydroxylase/C17,20-lyase (CYP17) inhibitor drug.

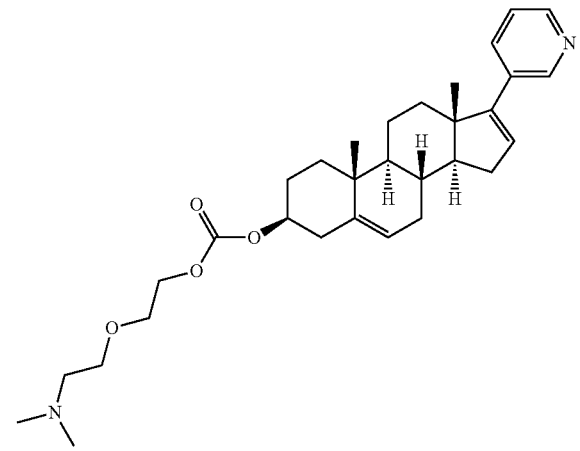

I

14 Claims, No Drawings

ABIRATERONE PRECURSOR COMPOUND AND PREPARATION METHOD AND USE THEREOF

CROSS REFERENCE TO THE RELATED APPLICATIONS

This application is the national phase entry of International Application No. PCT/CN2022/114763, filed on Aug. 25, 2022, which is based upon and claims priority to Chinese Patent Application No. 202110985807.5, filed on Aug. 26, 2021, the entire contents of which are incorporated herein by reference.

TECHNICAL FIELD

The present disclosure belongs to the field of precursor compounds, and specifically relates to an abiraterone precursor compound and a preparation method and use thereof.

BACKGROUND

Prostate cancer is the most prevalent malignant and lethal tumor worldwide, and an incidence rate of prostate cancer increases with an age. The current population aging trend has led to rapid growth of prostate cancer patients. An incidence rate of prostate cancer in China has grown rapidly in the past 10 years, and has ranked the sixth worldwide. An incidence rate of prostate cancer in the United States ranks the first worldwide, and a mortality rate of prostate cancer in the United States ranks the second worldwide. According to data of the American cancer society, about 218,000 men are diagnosed with prostate cancer and 32,000 men die from prostate cancer each year in the United States.

In China, prostate cancer used to be a relatively-rare disease, but in recent years, an incidence rate of prostate cancer has been on the rise. Epidemiological data show that an incidence rate of prostate cancer in China increased from 1.71/100,000 in 1993 to 7.9/100,000 in 2005. According to statistical data of the National Cancer Center in 2014, an incidence rate of prostate cancer in China is about 9.80/100,000, and is increasing at a rate of 10% per year. In other words, in 10 years, the incidence rate of prostate cancer in China may be doubled or even higher. As the aging of China's society becomes more and more serious, the incidence rate of prostate cancer in China may reach a peak in the next 10 years. China has a large population base with a high aging speed. Prostate cancer, as a male disease, will become increasingly common.

It has been proven that some diseases in a body are caused by a too-high androgen level, such as benign prostatic hyperplasia and prostate cancer. Androgens play an important role in the occurrence, growth, and spread of prostate cancer. Specifically, two major androgens are testosterone and dihydrotestosterone. 90% of testosterone is synthesized by testes, and the remaining 10% is synthesized by adrenal glands. Testosterone can be further converted into dihydrotestosterone with an increased activity under an action of a reductase (steroid 5α-reductase). Trace amounts of testosterone and dihydrotestosterone in a body can stimulate the growth of prostate cancer.

17α-hydroxylase/C17,20-lyase (CYP17) is a cytochrome P450 enzyme located in testes, adrenal glands, and other tissues such as prostate tumor tissues. CYP17 is a key enzyme in an androgen biosynthesis pathway, and has the following two consecutive reactions to catalyze the biosynthesis of testosterone: pregnenolone and progesterone are converted into 17α-hydroxyl derivatives under an action of 17α-hydroxylase, and then converted into dehydroisoandrosterone (DHEA) and androstenedione under an action of C17,20-lyase, respectively. DHEA and androstenedione both are androgens, and are precursors of testosterone. Testosterone can be further converted into dihydrotestosterone with an increased activity under an action of a reductase (steroid 5α-reductase).

If a tumor is confined merely to a prostate, the tumor can be removed through a surgery or a radiotherapy. About 15% of men with prostatic neoplasms undergo cancer spreads. There is currently no cure for these patients undergoing cancer spreads. A goal of a treatment is to prevent testes from producing testosterone and other androgens that are essential for the growth of prostate cancer cells. When a therapy such as radical prostatectomy or radiotherapy fails to cure a patient with prostate cancer, a drug treatment becomes a very important treatment.

CYP17 inhibitors can not only inhibit the biosynthesis of androgens in testes, but also inhibit the biosynthesis of androgens in adrenal glands and other tissues such as prostate tumor tissues. A CYP17 inhibitor treatment has a better therapeutic effect than the castration therapy commonly used in clinical practice that can only inhibit the biosynthesis of androgens in testes. A CYP17 inhibitor with high selectivity and a strong effect can be used to treat prostate cancer clinically by inhibiting an initial link of androgen biosynthesis and reducing an androgen level in a body.

Based on the above epidemiological and molecular biological knowledges, efforts to achieve the prevention and treatment of prostate cancer are of great urgency, and the research and development of CYP17 inhibitors is an important direction for a drug treatment of prostate cancer. As a novel CYP17 inhibitor, abiraterone acetate is developed by Centocor Ortho to treat prostate cancer. Abiraterone acetate was approved by the Food and Drug Administration (FDA) of the United States for marketing on Apr. 28, 2011, and a trade name of abiraterone acetate is Zytiga. Abiraterone acetate can be used in combination with prednisone to treat castration-resistant prostate cancer. On Jul. 28, 2011, Zytiga was approved by the Health Canada. In prostate cancer patients, testosterone can stimulate the growth of a tumor. Castration treatments, including drug or surgery treatments, can reduce the production of testosterone or block an action of testosterone, but these treatments cannot inhibit the production of androgens in other parts of a body, such that prostate cancer can continue to grow. Abiraterone can inhibit an activity of CYP17 for regulating the production of androgens in a targeted manner to reduce the production of androgens, thereby slowing down the growth of a tumor. Compared with a median survival time (10.9 months) of a patient treated with a combination of a placebo and prednisone, a median survival time (14.8 months) of a patient treated with a combination of abiraterone acetate and prednisone is prolonged by 3.9 months (p<0.0001), that is, a death risk is reduced by 35%.

Therefore, it is necessary to provide a novel abiraterone acetate prodrug to provide a new option for clinical practice.

SUMMARY

An objective of the present disclosure is to provide an abiraterone precursor compound and a preparation method and use thereof in view of the above-mentioned technical problems. The abiraterone precursor compound is a novel compound, which is comparable to abiraterone acetate and even superior to abiraterone acetate in some aspects. Therefore, the abiraterone precursor compound has a great market value.

To achieve the above objective of the present disclosure, the present disclosure adopts the following technical solutions:

The present disclosure provides a compound represented by formula I or a pharmaceutically acceptable salt thereof:

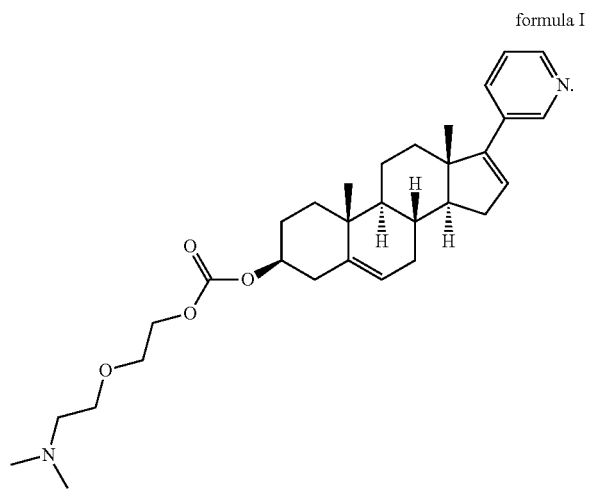

formula I

The present disclosure further provides a pharmaceutically acceptable salt of the compound represented by formula I, where the pharmaceutically acceptable salt of the compound represented by formula I has the following structural formula:

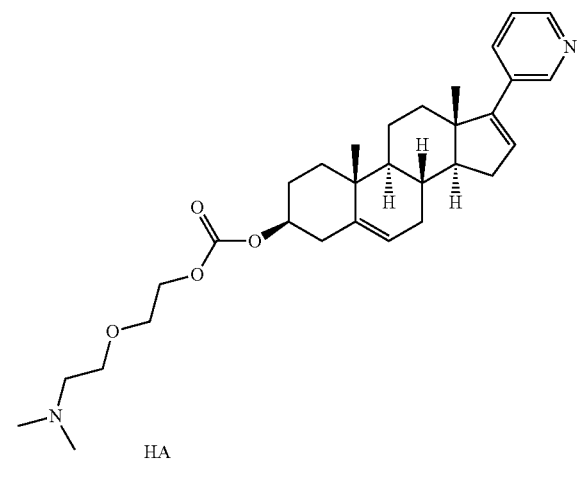

where HA is an inorganic acid or an organic acid.

Preferably, the pharmaceutically acceptable salt of the compound represented by formula I is selected from the group consisting of the following compounds:

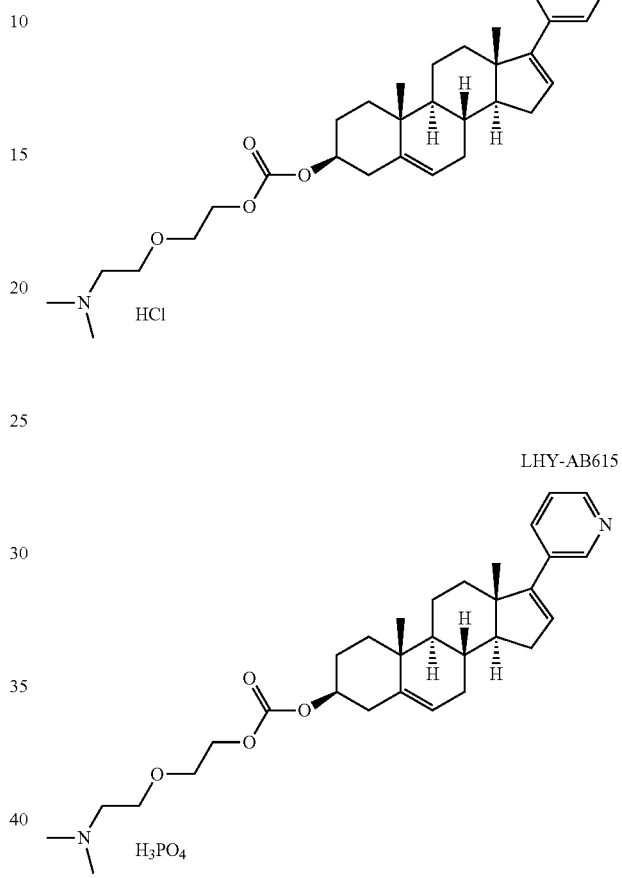

LHY-AB614

LHY-AB615

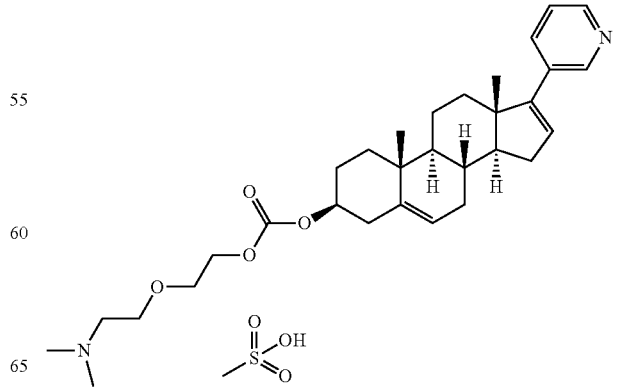

LHY-AB616

LHY-AB617

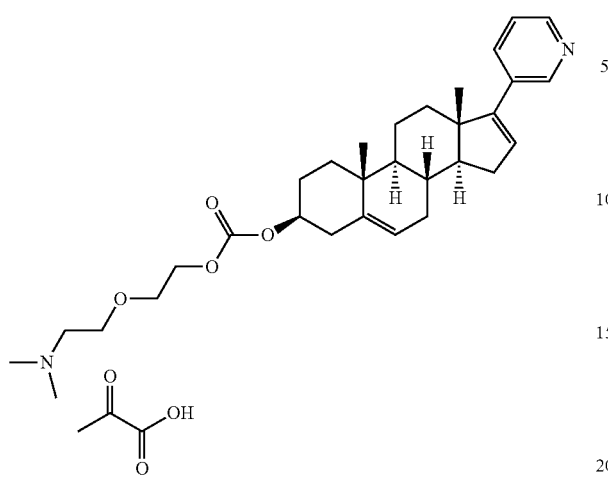

LHY-AB618

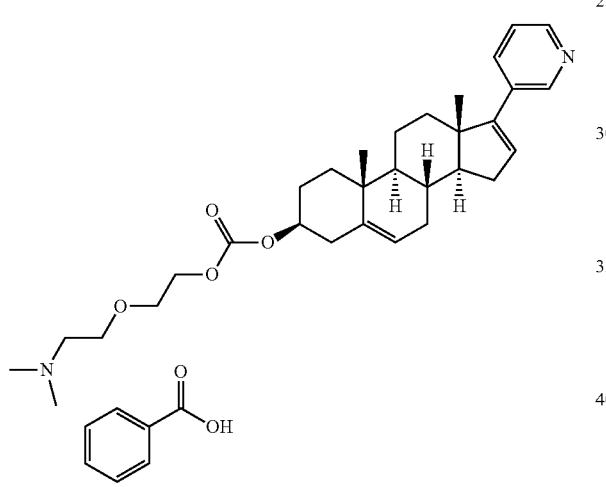

LHY-AB619

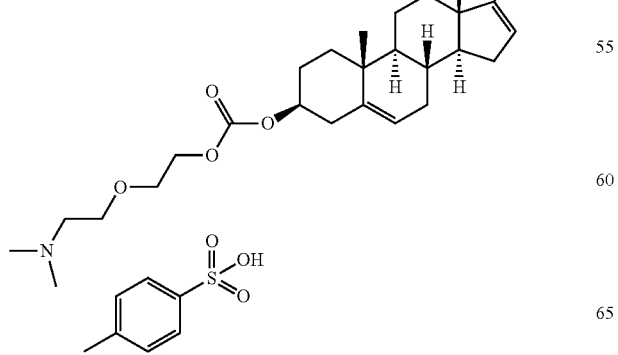

LHY-AB620

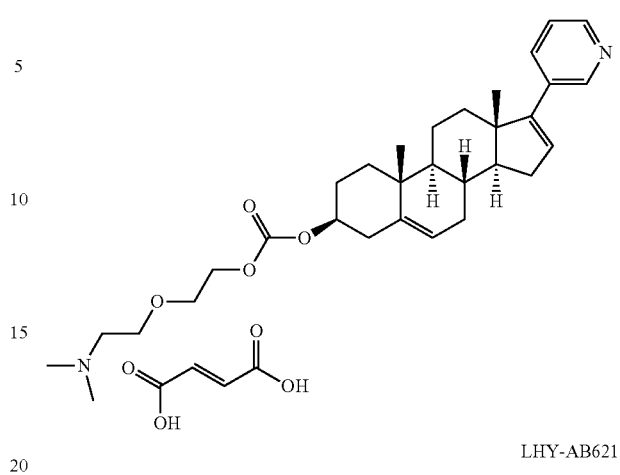

LHY-AB621

LHY-AB622

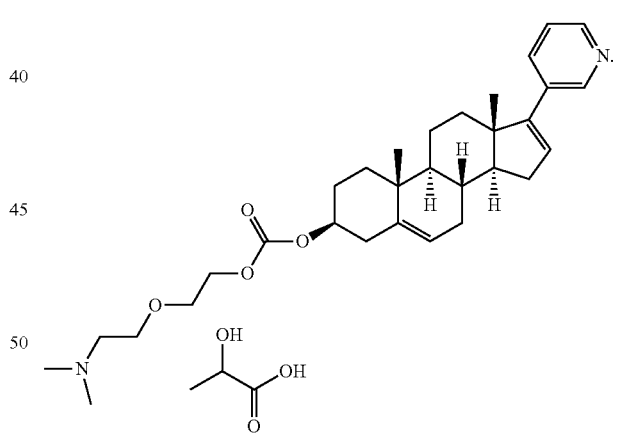

The present disclosure further provides a preparation method of the compound represented by formula I, including the following steps:

step 1: subjecting abiraterone to a first reaction with N,N'-carbonyldiimidazole in a solvent to obtain an intermediate Cpd-1; and step 2: subjecting the intermediate Cpd-1 to a second reaction with 2-[2-(dimethylamino)ethoxy]ethanol in the presence of a solvent and an alkali, and purifying a resulting product to obtain the compound represented by formula I.

The present disclosure further provides a preparation method of the pharmaceutically acceptable salt of the compound represented by formula I, including the following steps:

dissolving the compound represented by formula I in a solvent, and adding an equivalent amount of an acid to obtain the pharmaceutically acceptable salt of the compound represented by formula I; and refining the pharmaceutically acceptable salt.

A reaction flow of the preparation method of the compound represented by formula I and the pharmaceutically acceptable salt thereof is as follows:

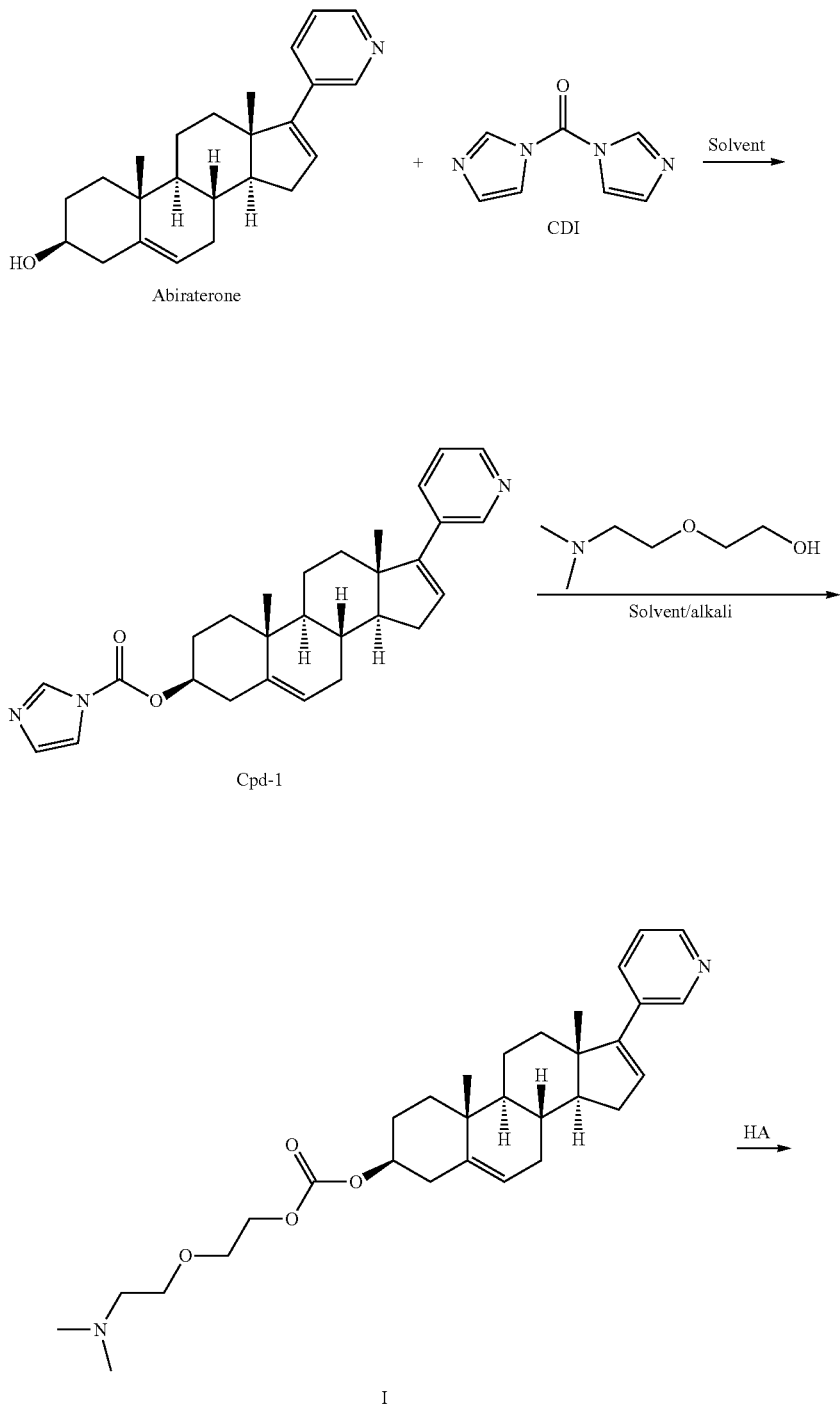

-continued

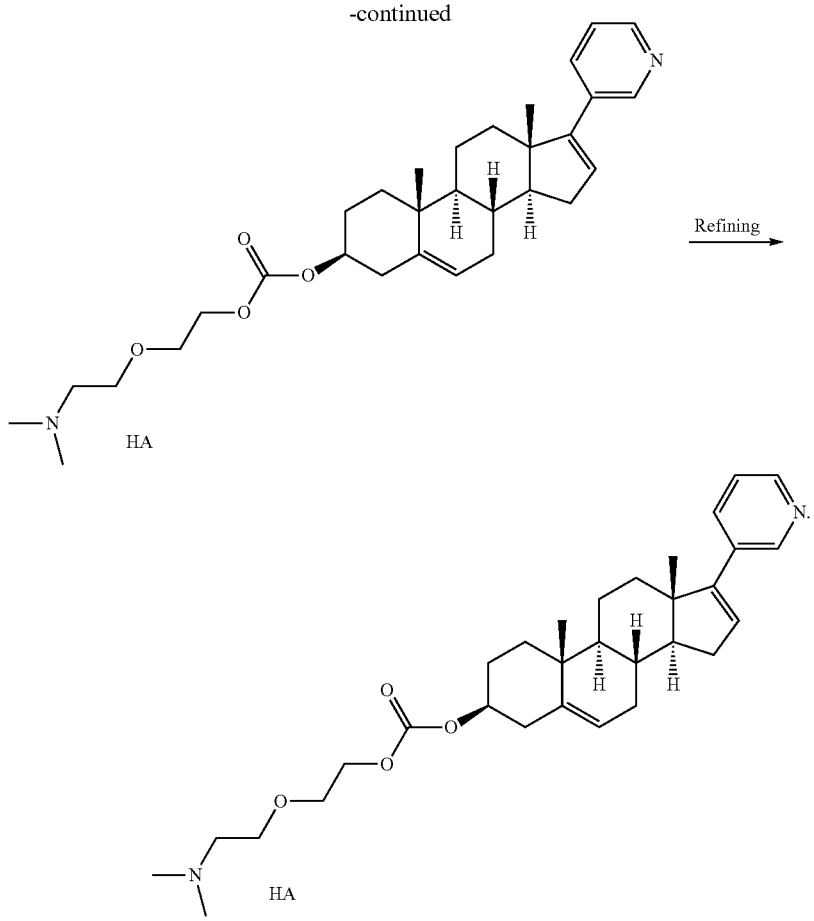

During the preparation process, a first reaction is preferably performed at room temperature (25° C.), and a reaction time of the first reaction is not particularly limited, and is usually 1 min to 24 h and preferably 1 h to 20 h. A first solvent used for the first reaction is usually selected from the group consisting of dichloromethane, acetone, ethyl acetate, N,N-dimethylformamide (DMF), dimethyl sulfoxide (DMSO), and pyridine. After the first reaction is completed, the first solvent is removed through concentration, a second solvent is added for crystallization, and a resulting crystallization system is subjected to suction filtration to obtain an intermediate. The second solvent is usually selected from the group consisting of tetrahydrofuran (THF), acetonitrile, petroleum ether, and methyl tert-butyl ether.

A second reaction is performed at room temperature to 100° C. and preferably at 60° C., and a reaction time of the second reaction is not particularly limited, and is usually 1 min to 24 h and preferably 1 h to 20 h. A third solvent used for the second reaction is usually selected from the group consisting of toluene, DMSO, dioxane, and THF. An alkali used for the second reaction is usually selected from the group consisting of sodium carbonate, sodium bicarbonate, potassium carbonate, sodium hydroxide, potassium hydroxide, triethylamine, and pyridine.

A third reaction is preferably performed at room temperature (25° C.), and a reaction time of the third reaction is not particularly limited, and is usually 1 min to 24 h and preferably 1 h to 20 h. A fourth solvent used for the third reaction is usually selected from the group consisting of dichloromethane, acetone, and ethyl acetate.

Refining is performed at −20° C. to 100° C. A fifth solvent used for the refining is usually selected from the group consisting of petroleum ether, ethyl acetate, methanol, ethanol, methyl tert-butyl ether, n-hexane, and THF.

The present disclosure provides a pharmaceutical composition including the compound represented by formula I or the pharmaceutically acceptable salt thereof.

Preferably, the pharmaceutical composition further includes one or more pharmaceutically acceptable carriers, diluents, or excipients.

The present disclosure also provides a use of the compound represented by formula I or the pharmaceutically acceptable salt thereof or the pharmaceutical composition in preparation of a CYP17 inhibitor drug.

The present disclosure also provides a use of the compound represented by formula I or the pharmaceutically acceptable salt thereof or the pharmaceutical composition in preparation of a drug for preventing or treating an androgen-associated disease.

Further, the androgen-associated disease includes a urogenital disease (such as urogenital cancer or prostatic hypertrophy) or other androgen-associated diseases (such as androgenetic alopecia and androgen-associated non-urogenital cancer); and the urogenital cancer includes prostate cancer, breast cancer, ovarian cancer, and other urogenital cancer.

An action mechanism of the compound of the present disclosure is as follows: It has been proved through animal experiments that the compound of the present disclosure has excellent prodrug properties, and can be rapidly absorbed in a body and then degraded into the active ingredient of abiraterone, and the remaining degradation products of the compound are chemically analyzed to be corresponding alcohols and carbon dioxide. Therefore, the compound of the present disclosure is safe and effective for a human body.

Compared with the prior art, the present disclosure has the following advantages.

1. Clinical studies have shown that, after being orally administered, abiraterone acetate, as a prodrug of abiraterone, can be absorbed by a human body, and deacetylated in the human body to obtain the active ingredient of abiraterone. The compound represented by formula I provided in the present disclosure also has prodrug properties, and can be rapidly absorbed in a body and then degraded into the active ingredient of abiraterone, and the remaining degradation products of the compound are corresponding alcohols and carbon dioxide. Therefore, the compound of the present disclosure is safe and effective.

2. It can be known from the in vitro cell proliferation toxicity experiment in Example 10 that $IC_{50}$ of the compound of the present disclosure is superior to $IC_{50}$ of the existing abiraterone acetate.

3. The pharmaceutically acceptable salt of the compound represented by formula I has excellent water solubility.

4. The comparative study of pharmacokinetic properties of Beagle dogs in Example 12 shows that the compound represented by formula I and abiraterone can both be detected in vivo after administration of LHY-AB614, and $C_{max}$ of abiraterone is much higher than $C_{max}$ of the compound represented by formula I. Only abiraterone is detected in vivo after administration of abiraterone acetate, indicating that abiraterone acetate is rapidly metabolized into abiraterone after entering a body. Compared with the administration of abiraterone acetate, when LHY-AB614 is orally administered, $C_{max}$ of abiraterone significantly increases, and $T_{max}$ does not change, indicating that the oral administration of the compound of the present disclosure can maintain a high plasma-drug concentration in vivo for a long period of time, which has great advantages in clinical practice. In addition, compared with the administration of abiraterone acetate, when LHY-AB614 is orally administered, an area under the curve (AUC) significantly increases, indicating that the compound of the present disclosure can significantly improve the bioavailability of oral administration.

DETAILED DESCRIPTION OF THE EMBODIMENTS

The technical solutions of the present disclosure are described in further detail below through specific examples, but it should be noted that the following examples are merely intended to describe the content of the present disclosure and do not constitute a limitation on the protection scope of the present disclosure.

Example 1 Synthesis of a Compound LHY-AB614

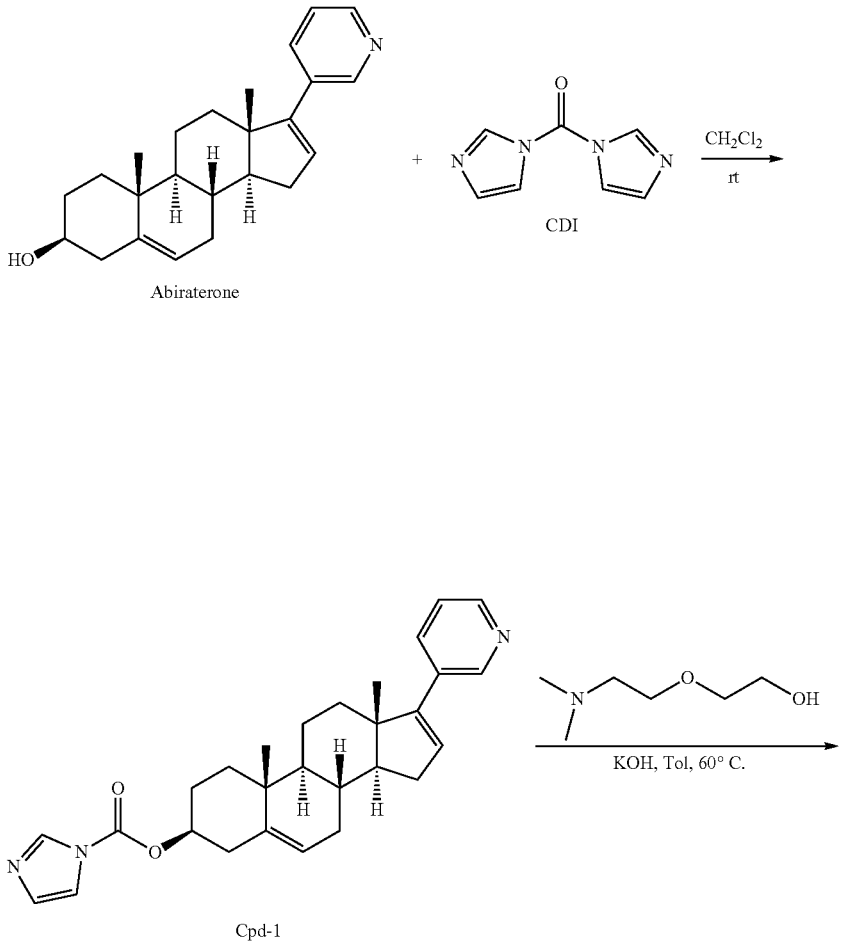

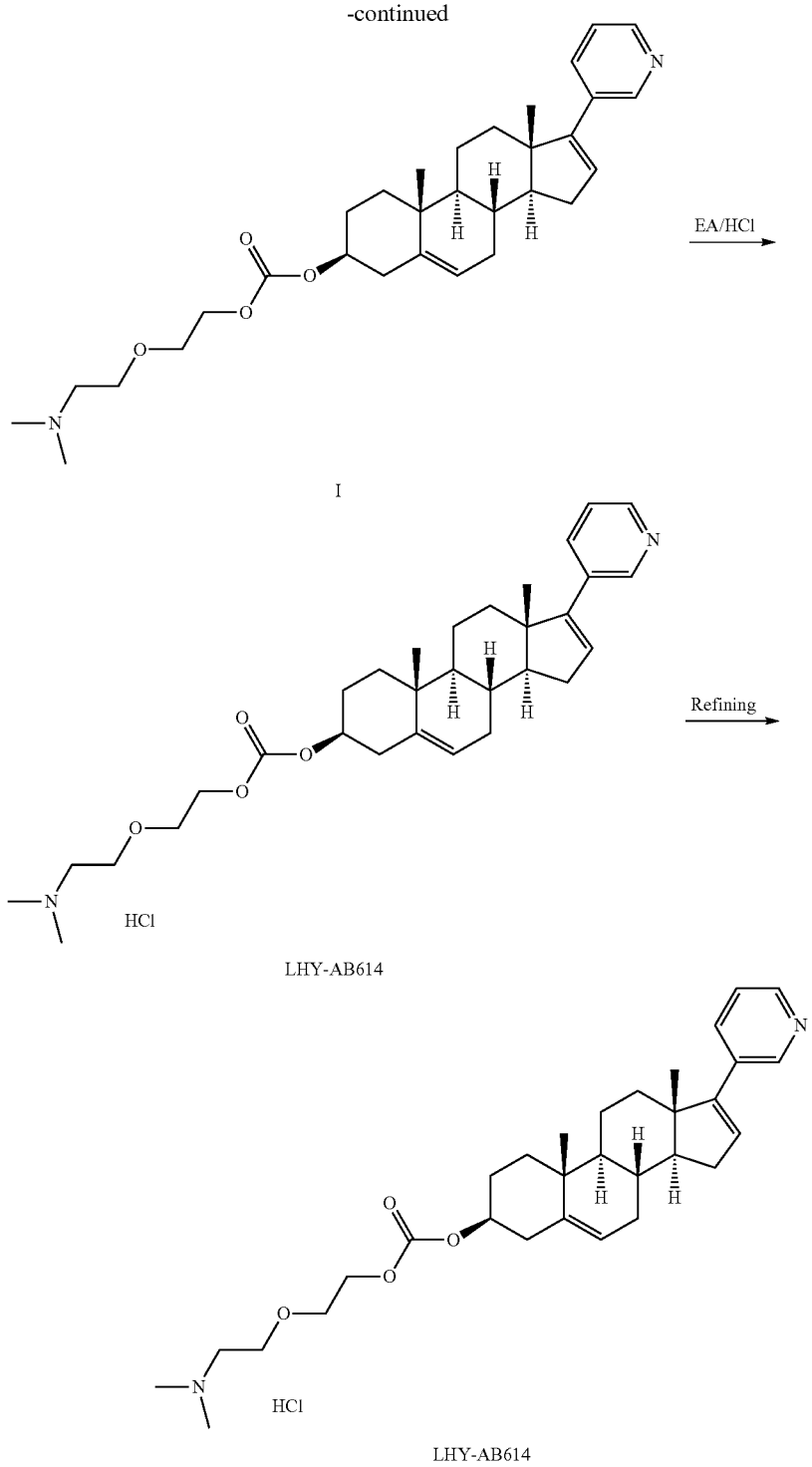

I

LHY-AB614

LHY-AB614

A dry 500 mL round-bottom flask was taken; abiraterone (10 g, 28.6 mmol, 1.0 eq) was added, 150 mL of $CH_2Cl_2$ was added for dissolution, CDI (14 g, 85.8 mmol, 3.0 eq) was added, and a first reaction was performed at room temperature for 8 h until it was detected by TLC (PE:EA=1:1) that the raw materials disappeared completely to obtain a first reaction system; the first reaction system was concentrated, 100 mL of dry THF was added to obtain a first mixture, and the first mixture was stirred for 30 min at room temperature and then subjected to first suction filtration to obtain a first filter cake; and the first filter cake was washed with dry THF (50 mL*3) and then dried to obtain a compound Cpd-1 (10 g, 22.6 mmol), with a yield of 79%.

A dry 250 mL round-bottom flask was taken; the compound Cpd-1 (10 g, 22.6 mmol, 1.0 eq) and KOH (250 mg, 4.5 mmol, 0.2 eq) were added, 100 mL of toluene was added, 2-[2-(dimethylamino)ethoxy]ethanol (4.1 mL, 29.4 mmol, 1.3 eq) was finally added, and a second reaction was performed overnight at 60° C. until it was detected by TLC that the raw materials disappeared completely to obtain a second reaction system; and the second reaction system was spin-dried to remove the solvent to obtain a solid compound, the solid compound was washed with water and subjected to extraction with $CH_2Cl_2$, and resulting organic phases were combined, dried, concentrated, and purified by column chromatography to obtain a compound represented by formula I (5.7 g, 11.2 mmol), with a yield of 49%. 1H NMR (400 MHZ, $CDCl_3$) δ 8.59 (s, 1H), 8.43 (d, J=3.9 Hz, 1H), 7.61 (d, J=7.8 Hz, 1H), 7.19 (dd, J=7.6, 4.9 Hz, 1H), 5.96 (s, 1H), 5.41 (d, J=3.5 Hz, 1H), 4.52-4.40 (m, 1H), 4.31-4.19 (m, 2H), 3.72-3.61 (m, 2H), 3.57 (t, J=5.7 Hz, 2H), 2.50 (t, J=5.6 Hz, 2H), 2.44-2.33 (m, 2H), 2.25 (s, 7H), 2.08-1.98 (m, 3H), 1.94-1.84 (m, 2H), 1.81-1.35 (m, 8H), 1.16-1.08 (m, 1H), 1.04 (s, 3H), 1.02 (s, 3H). 13C NMR (101 MHz, $CDCl_3$) δ 154.57, 151.69, 148.00, 147.96, 139.77, 133.70, 132.97, 129.27, 123.08, 122.65, 77.83, 69.33, 68.83, 66.73, 58.77, 57.51, 50.25, 47.36, 45.91, 38.09, 36.82, 36.78, 35.23, 31.85, 31.56, 30.43, 27.70, 20.88, 19.28, 16.65. EI-MS: m/z calcd for $C_{31}H_{44}N_2O_4$ $[M+H]^+$ 508.7 Found: 509.3.

The compound represented by formula I (10 g) was dissolved in 100 mL of ethyl acetate at room temperature, and a dried HCl gas was introduced to perform a third reaction; and after the third reaction was completed, 100 mL of petroleum ether was added to precipitate a solid LHY-AB614, a resulting supernatant was discarded, and the solid was dried to obtain a crude product LHY-AB614.

The crude product LHY-AB614 (1 g) was dissolved in 1.2 mL of methanol at room temperature, 25 mL of THF was slowly added dropwise to obtain a second mixture, and the second mixture was vigorously stirred at room temperature for precipitating a white solid to obtain a third reaction system; and the third reaction system was subjected to second suction filtration to obtain a second filter cake, and the second filter cake was dried to obtain pure LHY-AB614 (800 mg, purity: 99.6%).

Example 2 Synthesis of a Compound LHY-AB615

The compound represented by formula I (1 g) was dissolved in 10 mL of ethyl acetate at room temperature, and an equivalent amount of phosphoric acid was added to perform a reaction; and after the reaction was completed, 20 mL of petroleum ether was added for precipitating a solid LHY-AB615 to obtain a first reaction system, the first reaction system was subjected to first suction filtration to obtain a first filter cake, and the first filter cake was dried to obtain a crude product LHY-AB615.

The crude product LHY-AB615 (1 g) was dissolved in 1.2 mL of methanol at room temperature, 25 mL of THF was slowly added dropwise, and a resulting mixture was vigorously stirred at room temperature for precipitating a white solid to obtain a second reaction system; and the second reaction system was subjected to second suction filtration to obtain a second filter cake, and the second filter cake was dried to obtain pure LHY-AB615 (820 mg, purity: 99.5%).

Example 3 Synthesis of a Compound LHY-AB616

The compound represented by formula I (1 g) was dissolved in 10 mL of ethyl acetate at room temperature, and an equivalent amount of methanesulfonic acid was added to perform a reaction; and after the reaction was completed, 20 mL of petroleum ether was added for precipitating a solid LHY-AB616 to obtain a first reaction system, the first reaction system was subjected to first suction filtration to obtain a first filter cake, and the first filter cake was dried to obtain a crude product LHY-AB616.

The crude product LHY-AB616 (1 g) was dissolved in 1.2 mL of methanol at room temperature, 25 mL of THF was slowly added dropwise, and a resulting mixture was vigorously stirred at room temperature for precipitating a white solid to obtain a second reaction system; and the second reaction system was subjected to second suction filtration to obtain a second filter cake, and the second filter cake was dried to obtain pure LHY-AB616 (790 mg, purity: 99.7%).

Example 4 Synthesis of a Compound LHY-AB617

The compound represented by formula I (1 g) was dissolved in 10 mL of acetone at room temperature, and an equivalent amount of pyruvic acid was added to perform a reaction; and after the reaction was completed, 20 mL of petroleum ether was added for precipitating a solid LHY-AB617 to obtain a first reaction system, the first reaction system was subjected to first suction filtration to obtain a first filter cake, and the first filter cake was dried to obtain a crude product LHY-AB617.

The crude product LHY-AB617 (1 g) was dissolved in 1.2 mL of methanol at room temperature, 25 mL of THF was slowly added dropwise, and a resulting mixture was vigorously stirred at room temperature for precipitating a white solid to obtain a second reaction system; and the second reaction system was subjected to second suction filtration to obtain a second filter cake, and the second filter cake was dried to obtain pure LHY-AB617 (800 mg, purity: 99.7%).

Example 5 Synthesis of a Compound LHY-AB618

The compound represented by formula I (1 g) was dissolved in 10 mL of ethyl acetate at room temperature, and an equivalent amount of benzoic acid was added to perform a reaction; and after the reaction was completed, 20 mL of petroleum ether was added for precipitating a solid LHY-AB618 to obtain a first reaction system, the first reaction system was subjected to first suction filtration to obtain a first filter cake, and the first filter cake was dried to obtain a crude product LHY-AB618.

The crude product LHY-AB618 (1 g) was dissolved in 1.2 mL of methanol at room temperature, 25 mL of THF was slowly added dropwise, and a resulting mixture was vigorously stirred at room temperature for precipitating a white solid to obtain a second reaction system; and the second reaction system was subjected to second suction filtration to obtain a second filter cake, and the second filter cake was dried to obtain pure LHY-AB618 (820 mg, purity: 99.6%).

Example 6 Synthesis of a Compound LHY-AB619

The compound represented by formula I (1 g) was dissolved in 10 mL of ethyl acetate at room temperature, and an equivalent amount of p-toluenesulfonic acid was added to perform a reaction; and after the reaction was completed, 20 mL of petroleum ether was added for precipitating a solid LHY-AB619 to obtain a first reaction system, the first reaction system was subjected to first suction filtration to obtain a first filter cake, and the first filter cake was dried to obtain a crude product LHY-AB619.

The crude product LHY-AB619 (1 g) was dissolved in 1.2 mL of methanol at room temperature, 25 mL of THF was slowly added dropwise, and a resulting mixture was vigorously stirred at room temperature for precipitating a white solid to obtain a second reaction system; and the second reaction system was subjected to second suction filtration to obtain a second filter cake, and the second filter cake was dried to obtain pure LHY-AB619 (800 mg, purity: 99.8%).

Example 7 Synthesis of a Compound LHY-AB620

The compound represented by formula I (1 g) was dissolved in 10 mL of ethyl acetate at room temperature, and an equivalent amount of maleic acid was added to perform a reaction; and after the reaction was completed, 20 mL of petroleum ether was added for precipitating a solid LHY-AB620 to obtain a first reaction system, the first reaction system was subjected to first suction filtration to obtain a first filter cake, and the first filter cake was dried to obtain a crude product LHY-AB620.

The crude product LHY-AB620 (1 g) was dissolved in 1.2 mL of methanol at room temperature, 25 mL of THF was slowly added dropwise, and a resulting mixture was vigorously stirred at room temperature for precipitating a white solid to obtain a second reaction system; and the second reaction system was subjected to second suction filtration to obtain a second filter cake, and the second filter cake was dried to obtain pure LHY-AB620 (840 mg, purity: 99.7%).

Example 8 Synthesis of a Compound LHY-AB621

The compound represented by formula I (1 g) was dissolved in 10 mL of ethyl acetate at room temperature, and an equivalent amount of succinic acid was added to perform a reaction; and after the reaction was completed, 20 mL of petroleum ether was added for precipitating a solid LHY-AB621 to obtain a first reaction system, the first reaction system was subjected to first suction filtration to obtain a first filter cake, and the first filter cake was dried to obtain a crude product LHY-AB621.

The crude product LHY-AB621 (1 g) was dissolved in 1.2 mL of methanol at room temperature, 25 mL of THF was slowly added dropwise, and a resulting mixture was vigorously stirred at room temperature for precipitating a white solid to obtain a second reaction system; and the second reaction system was subjected to second suction filtration to obtain a second filter cake, and the second filter cake was dried to obtain pure LHY-AB621 (830 mg, purity: 99.8%).

Example 9 Synthesis of a Compound LHY-AB622

The compound represented by formula I (1 g) was dissolved in 10 mL of ethyl acetate at room temperature, and an equivalent amount of malic acid was added to perform a reaction; and after the reaction was completed, 20 mL of petroleum ether was added for precipitating a solid LHY-AB622 to obtain a first reaction system, the first reaction system was subjected to first suction filtration to obtain a first filter cake, and the first filter cake was dried to obtain a crude product LHY-AB622.

The crude product LHY-AB622 (1 g) was dissolved in 1.2 mL of methanol at room temperature, 25 mL of THF was slowly added dropwise, and a resulting mixture was vigorously stirred at room temperature for precipitating a white solid to obtain a second reaction system; and the second reaction system was subjected to second suction filtration to obtain a second filter cake, and the second filter cake was dried to obtain pure LHY-AB622 (810 mg, purity: 99.7%).

Example 10 Cell Viability Test of Abiraterone Carboxylate Prodrugs

Half-maximal inhibitory concentrations ($IC_{50}$) of abiraterone acetate and LHY-AB614 for proliferation of LNCAP clone FGC and VCAP were assessed by a CellTiter-Glo® chemiluminescent cell viability assay (namely, a CTG method).

Cells in an exponential phase were collected, and live cells were counted. Each cell suspension was adjusted with a corresponding medium to an appropriate concentration. 90 µL of a cell suspension was added to each well of a 96-well plate and cultivated in a 37° C. and 5% $CO_2$ incubator for 24 h.

A sample to be tested was dissolved in DMSO to prepare a stock solution with a starting concentration of 50 µM, and the stock solution was 3-fold diluted with a medium to obtain 10× working solutions with 9 concentrations. Cisplatin, as a reference compound, was dissolved in DMSO to prepare a stock solution with a starting concentration of 100 µM, and the stock solution was 3-fold diluted with a medium to obtain 10× working solutions with 9 concentrations. 10 µL of a working solution was added to cells in each well, and then the cells were cultivated in a 37° C. and 5% $CO_2$ incubator for 72 h.

The 96-well plate was equilibrated at room temperature for about 30 min, then 50 µL of a CTG solution was added to each well, and the 96-well plate was shaken on a microplate shaker for 2 min to perform cell lysis and placed at room temperature for 20 min to stabilize a fluorescence signal. A fluorescence signal value was determined with an Envision2104 plate reader. On the GraphPad Prism software, a nonlinear regression model was used to plot an S-type dose-response curve and calculate an $IC_{50}$ value. Results are shown in Table 1. $IC_{50}$ values of LHY-AB614 for LNCAP and VCAP cells were 3.2 µM and 5.7 µM, respectively, which were significantly better than an $IC_{50}$ value of abiraterone acetate.

TABLE 1

Inhibition of the test compounds and the control compound on LNCAP and VCAP cells

| Cell Line Name | Test Article | Absolute $IC_{50}$(µM) | Max inhibition |
|---|---|---|---|
| LNCAP | Compound represented by formula I | 3.2 | 99.49% |
| | Abiraterone acetate | 15.5 | 78.30% |
| | Cisplatin | 12.8 | 97.49% |
| VCAP | Compound represented by formula I | 5.7 | 99.31% |
| | Abiraterone acetate | >50 | 29.43% |
| | Cisplatin | 40.3 | 85.02% |

Example 11 Solubility Test of LHY-AB614-622

200 mg of LHY-AB614-622 was weighed, and 1 mL of normal saline was added. Test results show that LHY-AB614-622 can be well dissolved, indicating that LHY-AB614-622 has an excellent solubility in normal saline, which is higher than 200 mg/mL.

2 mg of abiraterone acetate was weighed and dissolved in 1 mL of normal saline, a resulting solution was stirred overnight and then subjected to suction filtration, and a resulting filtrate was subjected to HPLC analysis. Abiraterone acetate was dissolved in methanol to prepare a 0.1 mg/mL solution as a control. Test results show that abiraterone acetate is extremely insoluble in water, and has a solubility of less than 0.1 mg/mL in normal saline.

Example 12 Comparative Study of Pharmacokinetic Properties of LHY-AB614 in Beagle Dogs In order to prove that the LHY-AB614 of the present disclosure is superior to the existing abiraterone acetate in terms of bioavailability in vivo, abiraterone acetate was used as a reference drug to evaluate bioavailability and bioequivalence. Four healthy Beagle dogs with body weights in a range of 6 kg to 8 kg were selected. The Beagle dogs were fasted for 12 h the day before an experiment, and all were given a low-fat standard meal after administration. The Beagle dogs should not be administered with other drugs two weeks before the experiment and during the experiment. The four Beagle dogs were randomly divided into a group A and a group B (2 dogs in each group).

LHY-AB614 was administered orally at a dose of 46.8 mg/kg (32.2 mg/kg based on abiraterone), and abiraterone acetate was administered orally at a dose of 42.3 mg/kg (37.8 mg/kg based on abiraterone). Blank blood was collected in an EDTA-K2 anticoagulation tube before administration, and at 0.25 h, 0.5 h, 1.0 h, 2.0 h, 4.0 h, 6.0 h, 8.0 h, and 24.0 h after administration, 1 mL of blood was collected in EDTA-K2 anticoagulation tubes. After blood was fully mixed with an anticoagulant, each of the anticoagulation tubes was immediately placed in ice and centrifuged as soon as possible to isolate plasma, and the isolated plasma was stored in labeled EP tubes. 50 μL of a plasma sample was taken, 300 μL of a 10 ng/mL carbamazepine-containing acetonitrile solution was added for protein precipitation, and a resulting mixture was vortexed for 5 min and then centrifuged in a centrifuge at 5,500 g for 10 min; and 100 μL of a resulting supernatant was taken, 300 μL of 50%-methanol water was added for dilution, a resulting dilution was vortexed, and 5 μL of a vortexed dilution was injected. In vivo drug concentrations of LHY-AB614, abiraterone acetate, and abiraterone were determined by HPLC-MS/MS.

TABLE 2

Pharmacokinetic parameters of LHY-AB614 and abiraterone in plasma of Beagle dogs orally administered with LHY-AB614

| PK parameters | $C_{max}$ | $T_{max}$ (h) | $T_{1/2}$ (h) | $Cl_{s,\,app}$ | $AUC_{0-t}$ (ng · h/mL) | $AUC_{0-inf}$ (ng · h/mL) | MRT (h) |
|---|---|---|---|---|---|---|---|
| Detection of LHY-AB614 | 223 | 1.5 | 6.8 | 757 | 908 | 1063 | 8.8 |
| Detection of abiraterone | 1114 | 1.5 | 3.7 | 132 | 6116 | 6186 | 5.8 |

TABLE 3

Pharmacokinetic parameters of abiraterone in plasma of Beagle dogs orally administered with abiraterone acetate

| PK parameters | $C_{max}$ | $T_{max}$ (h) | $T_{1/2}$ (h) | $Cl_{s,\,app}$ | $AUC_{0-t}$ (ng · h/mL) | $AUC_{0-inf}$ (ng · h/mL) | MRT (h) |
|---|---|---|---|---|---|---|---|
| Detection of abiraterone | 527 | 1.5 | 8.16 | 222 | 2293 | 3034 | 11.9 |

The results show that, after LHY-AB614 is administered, LHY-AB614 and abiraterone both can be detected in vivo, and $C_{max}$ of abiraterone is much higher than $C_{max}$ of LHY-AB614. Only abiraterone is detected in vivo after administration of abiraterone acetate, indicating that abiraterone acetate is rapidly metabolized into abiraterone after entering a body. Compared with the administration of abiraterone acetate, when LHY-AB614 is orally administered, $C_{max}$ of abiraterone significantly increases, and $T_{max}$ does not change, indicating that the oral administration of the compound of the present disclosure can maintain a high plasma-drug concentration in vivo for a long period of time, which has great advantages in clinical practice. In addition, compared with the administration of abiraterone acetate, when LHY-AB614 is orally administered, AUC significantly increases, indicating that the compound of the present disclosure can significantly improve the bioavailability of oral administration.

What is claimed is:

1. A compound represented by formula I or a pharmaceutically acceptable salt thereof:

formula I

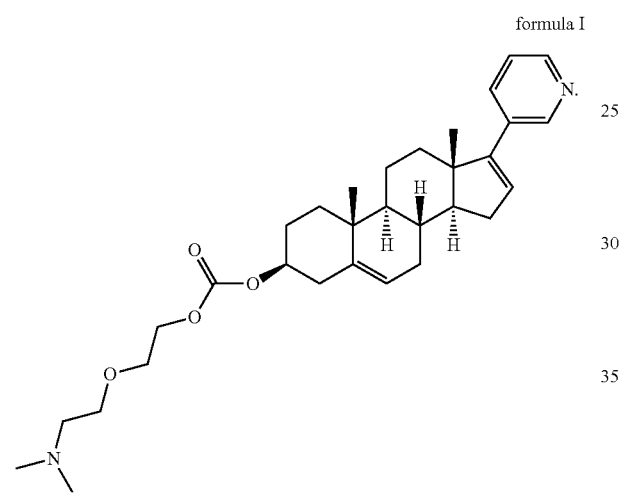

formula I, wherein the compound represented by formula I has a solubility in normal saline of 200 mg/mL or higher.

2. A pharmaceutically acceptable salt of the compound represented by the formula I according to claim 1, having the following structural formula:

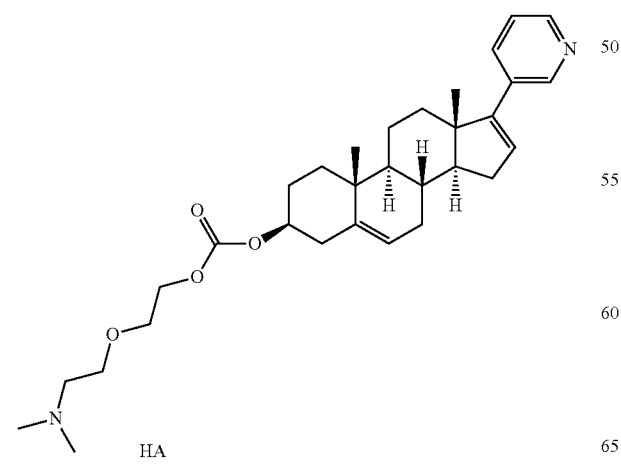

wherein HA is an inorganic acid or an organic acid; and wherein, the pharmaceutically acceptable salt of the compound represented by the formula I is selected from the group consisting of the following compounds:

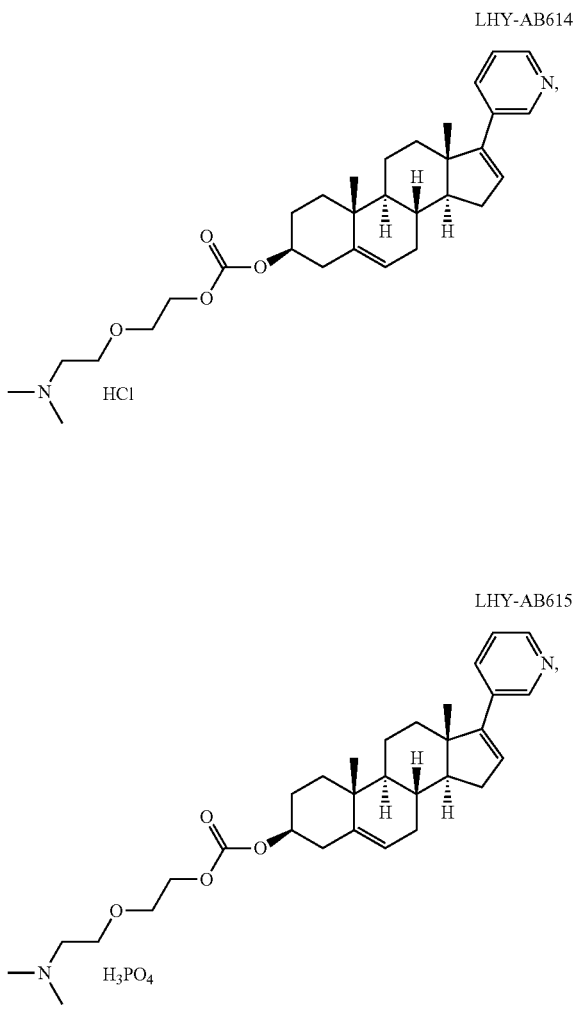

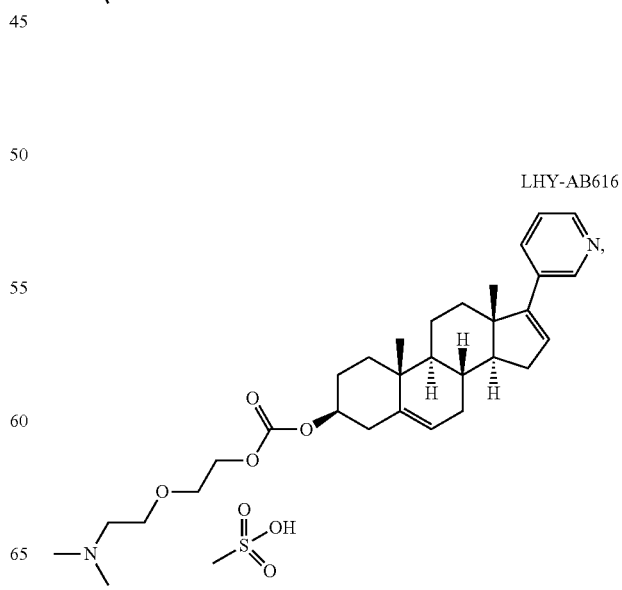

LHY-AB617
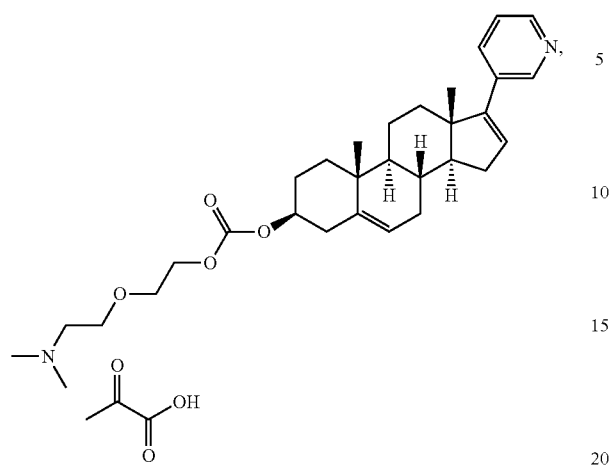
LHY-AB618
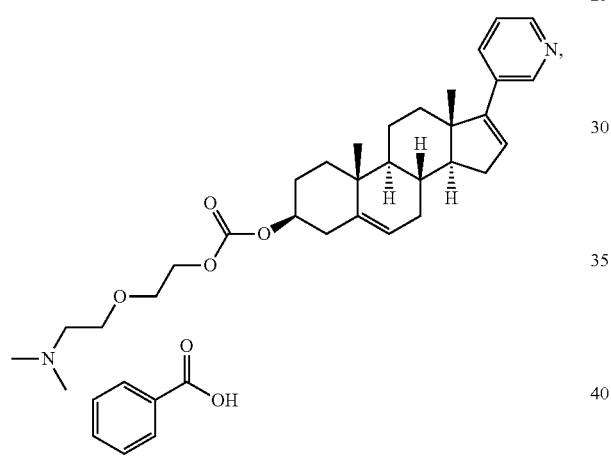
LHY-AB619
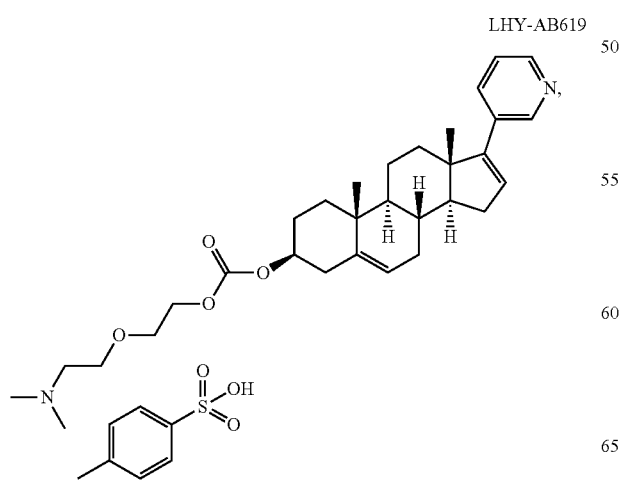
LHY-AB620
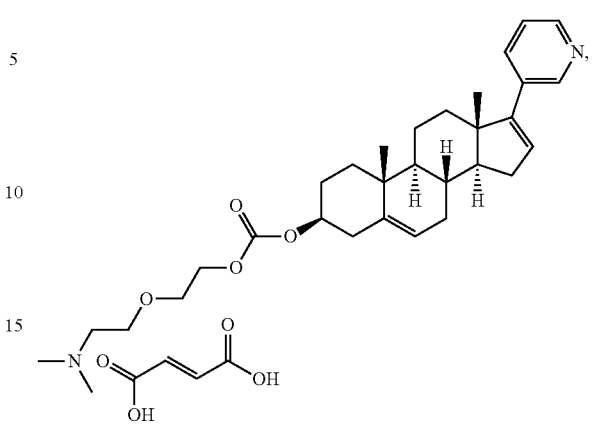
LHY-AB621, and
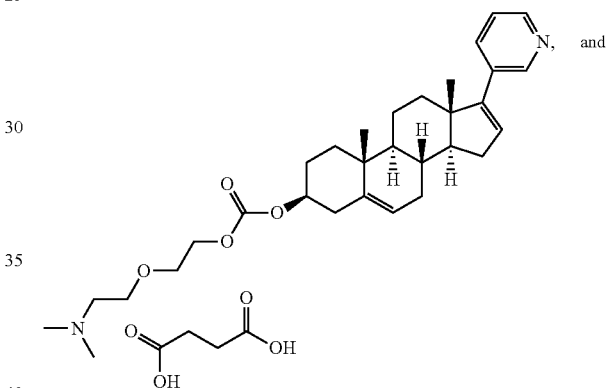
LHY-AB622
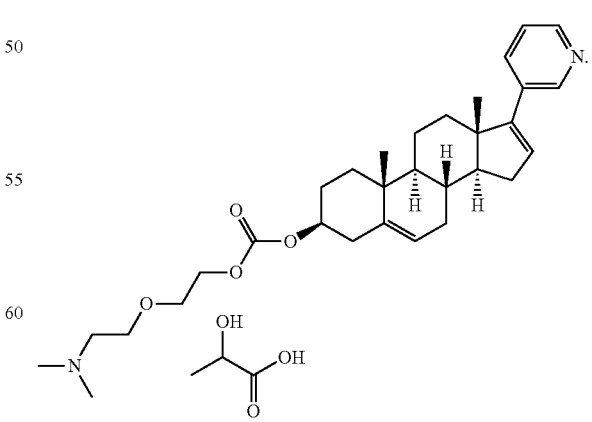

3. A pharmaceutically acceptable salt of the compound represented by the formula I according to claim 1, having the following structural formula:

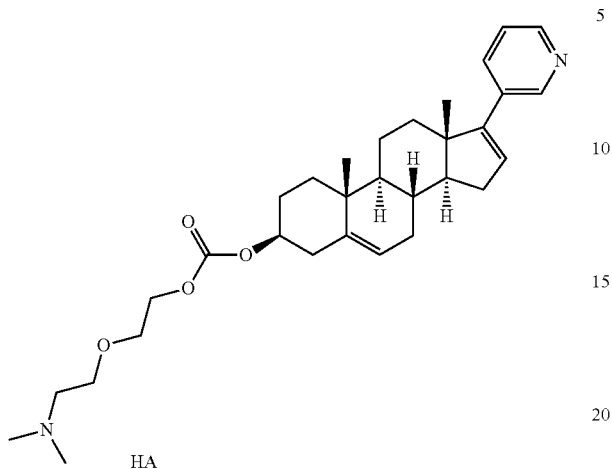

wherein HA is HCl.

4. A pharmaceutical composition comprising the compound represented by the formula I or the pharmaceutically acceptable salt thereof according to claim 1.

5. A preparation method of the compound represented by the formula I according to claim 1, comprising the following steps:

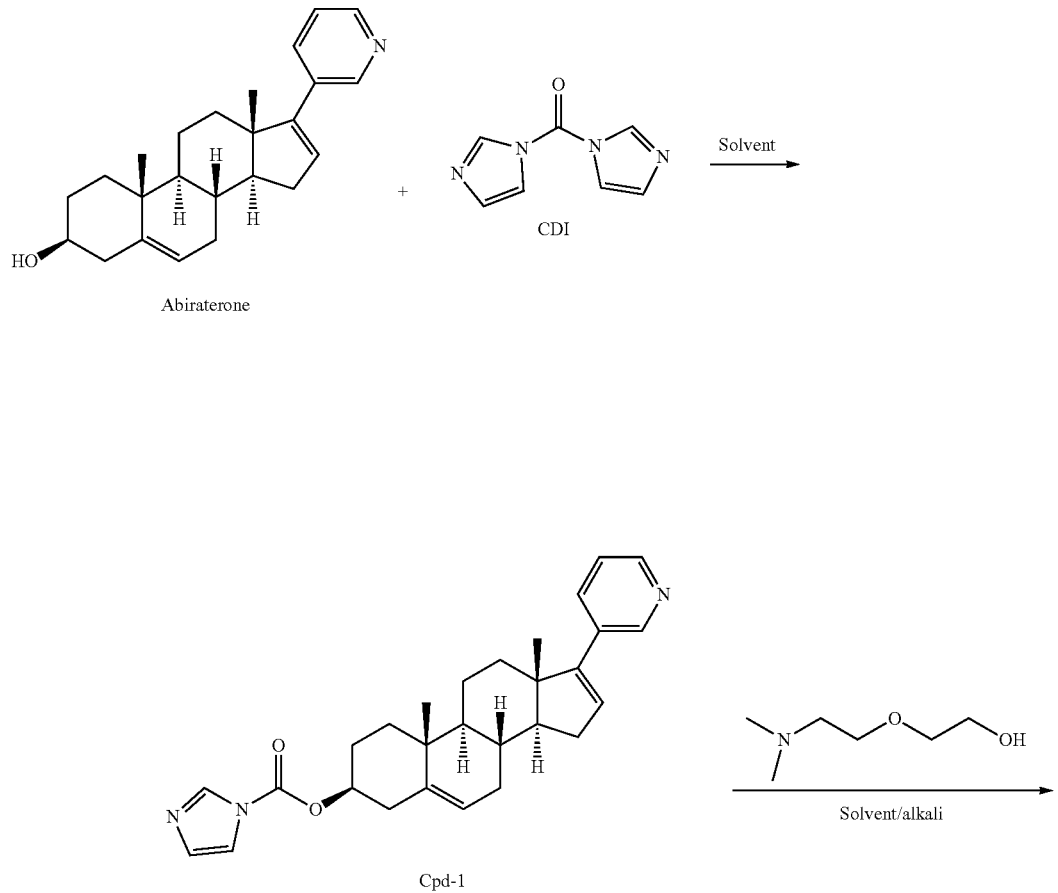

-continued

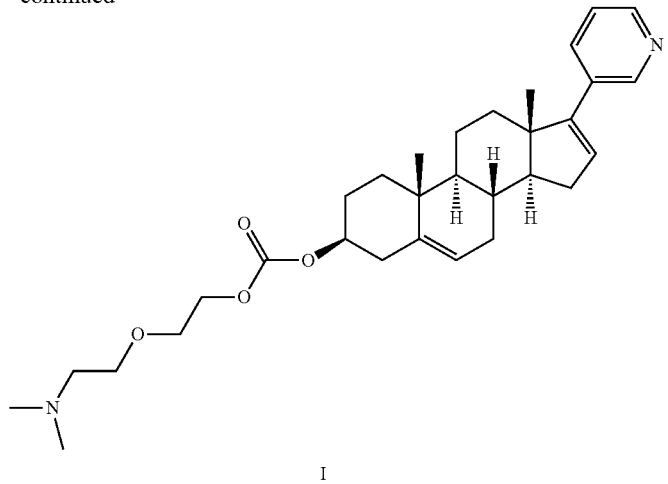

I step 1: subjecting abiraterone to a first reaction with N,N'-carbonyldiimidazole in a first solvent to obtain an intermediate Cpd-1; and step 2: subjecting the intermediate Cpd-1 to a second reaction with 2-[2-(dimethylamino)ethoxy]ethanol in the presence of a second solvent and an alkali to obtain the compound represented by the formula I.

6. The preparation method according to claim 5, wherein in the step 1, the first reaction is performed at 20° C. to 30° C. for 1 min to 24 h, and the first solvent is one or a mixture of two or more selected from the group consisting of dichloromethane, acetone, ethyl acetate, N,N-dimethylformamide (DMF), dimethyl sulfoxide (DMSO), and pyridine; and in the step 2, the second reaction is performed at 20° C. to 100° C. for 1 min to 24 h, the second solvent is one or a mixture of two or more selected from the group consisting of toluene, DMSO, dioxane, and tetrahydrofuran, and the alkali is selected from the group consisting of sodium carbonate, sodium bicarbonate, potassium carbonate, sodium hydroxide, potassium hydroxide, triethylamine, and pyridine.

7. A preparation method of the pharmaceutically acceptable salt of the compound represented by the formula I according to claim 2, comprising the following steps:

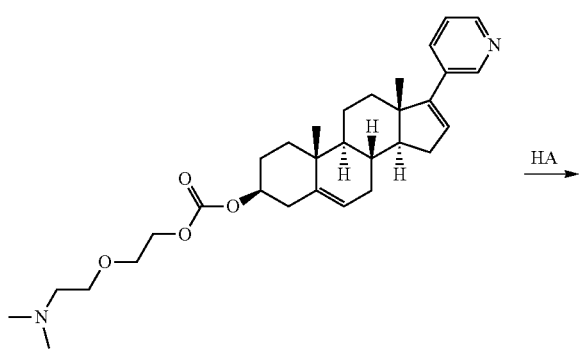

I $\xrightarrow{\text{HA}}$

-continued

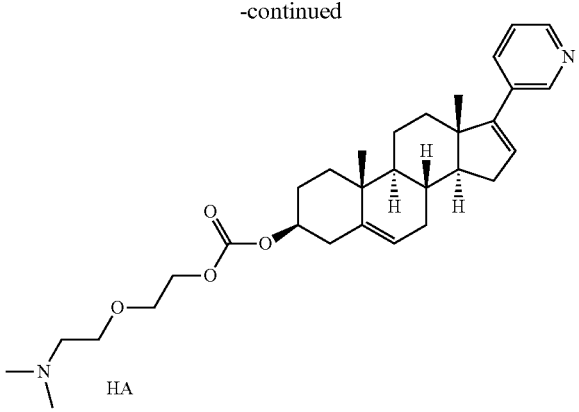

HA dissolving the compound represented by the formula I in a solvent, adding an equivalent amount of an acid HA, and performing a reaction to obtain the pharmaceutically acceptable salt of the compound represented by the formula I, wherein the acid HA is the same as the HA as defined in claim 2.

8. The preparation method of the pharmaceutically acceptable salt of the compound represented by the formula I according to claim 7, wherein the reaction is performed at 20° C. to 30° C. for 1 min to 24 h, and the solvent is one or a mixture of two or more selected from the group consisting of dichloromethane, acetone, and ethyl acetate.

9. A method for inhibiting 17α-hydroxylase/C17,20-lyase (CYP17) comprising the step of administering the compound or the pharmaceutically acceptable salt thereof according to claim 1.

10. A method for preventing or treating an androgen-associated disease comprising the step of administering the compound or the pharmaceutically acceptable salt thereof according to claim 1.

11. The method according to claim 10, wherein the androgen-associated disease is a urogenital disease, wherein the urogenital disease comprises urogenital cancer or prostatic hypertrophy; and the urogenital cancer is prostate cancer, breast cancer, or ovarian cancer.

12. A method for inhibiting 17α-hydroxylase/C17,20-lyase (CYP17) comprising the step of administering the pharmaceutical composition according to claim 4.

13. A method for preventing or treating an androgen-associated disease comprising the step of administering the pharmaceutical composition according to claim 4.

14. The method according to claim 13, wherein the androgen-associated disease is a urogenital disease, wherein the urogenital disease comprises urogenital cancer or prostatic hypertrophy; and the urogenital cancer is prostate cancer, breast cancer, or ovarian cancer.

* * * * *